United States Patent [19]

Svensson et al.

[11] Patent Number: 5,593,444
[45] Date of Patent: Jan. 14, 1997

[54] SPACING MEMBER FOR ATTACHING CRANIAL FACIAL PROSTHESIS

[75] Inventors: Thomas Svensson, Göteborg; Bo Rangert, Mönlycke; Kerstin Jansson, Frölunda; Einar Jörgensen, Hisingskärra, all of Sweden

[73] Assignee: Nobelpharma AB, Gothenburg, Sweden

[21] Appl. No.: 265,822

[22] Filed: Jun. 27, 1994

Related U.S. Application Data

[63] Continuation of Ser. No. 38,186, Mar. 29, 1993, abandoned, which is a continuation of Ser. No. 827,451, Jan. 29, 1992, abandoned.

[30] Foreign Application Priority Data

Jan. 29, 1991 [SE] Sweden .................. 9100256

[51] Int. Cl.⁶ .................................................. A61F 2/14
[52] U.S. Cl. .................................................. 623/16; 623/4
[58] Field of Search .................. 623/4, 18, 16; 606/64, 72; 403/205, 403; D24/155, 157; 433/201.1

[56] References Cited

U.S. PATENT DOCUMENTS

| D. 294,295 | 2/1988 | Branemark ............... D24/155 |
|---|---|---|
| 641,118 | 1/1900 | Kelly ...................... 403/403 X |
| 1,077,560 | 11/1913 | Ryan ...................... 623/18 |
| 2,572,416 | 10/1951 | Wilson . | 
| 3,488,779 | 1/1970 | Christensen ............. 623/18 |
| 3,871,783 | 3/1975 | Vogler .................... 403/205 |
| 3,906,550 | 9/1975 | Rostoker et al. ........ 623/18 X |
| 4,014,618 | 3/1977 | Kristiansen ............. 403/205 |
| 4,087,867 | 5/1978 | Hickmann et al. . | 
| 4,281,649 | 8/1981 | Derweduwen ........... 606/64 |
| 4,379,694 | 4/1983 | Riess ...................... 433/201.1 |
| 4,676,802 | 6/1987 | Tofield . | 
| 4,936,853 | 6/1990 | Fabian et al. ........... 623/20 |
| 5,041,139 | 8/1991 | Branemark .............. 623/21 |
| 5,069,622 | 12/1991 | Rangert et al. ......... 433/173 |
| 5,085,660 | 2/1992 | Lin ......................... 606/73 |

FOREIGN PATENT DOCUMENTS

| 0179695 | 4/1986 | European Pat. Off. ........ 623/17 |
|---|---|---|
| 1063329 | 5/1954 | France .................. 623/4 |
| 2647666 | 12/1990 | France . |
| 3434949 | 5/1986 | Germany . |
| 0623238 | 5/1949 | United Kingdom ........ 623/4 |
| 83 02047 | 6/1983 | WIPO . |

*Primary Examiner*—David H. Willse
*Attorney, Agent, or Firm*—Pollock, Vande Sande & Priddy

[57] ABSTRACT

The invention relates to a spacing member arranged between a securing element (fixture) implanted in the facial bone (the cranium) and an extraoral prosthesis, in particular a facial prosthesis. The spacing member comprises a base portion (1) intended to cooperate with the upper portion of the securing element, and an extension part (8, 8') which forms an attachment point for the prosthesis. The extension part (8, 8') is designed in such a way that it permits attachment of the prosthesis in a direction (attachment direction) which forms essentially a right angle to the longitudinal direction of the extension part. The spacing member combines the two conflicting requirements which exist particularly in the case of an orbital prosthesis, namely secure anchoring in the bone (radial attachment of the securing elements) and a more favorable attachment direction (axial) for the prosthetic work.

13 Claims, 2 Drawing Sheets

SPACING MEMBER FOR ATTACHING CRANIAL FACIAL PROSTHESIS

This application is a continuation of Ser. No. 08/038,186 filed on Mar. 29, 1993 now abandoned; which is a continuation of Ser. No. 07/827,451 filed Jan. 29, 1992, now abandoned.

FIELD OF THE INVENTION

The invention relates to a spacing member arranged between a securing element (fixture) implanted in the facial bone (the cranium) and an extraoral prosthesis, in particular a facial prosthesis.

BACKGROUND OF THE INVENTION

It is already known to permanently anchor oral prostheses in the jawbone with the aid of screw-shaped securing elements, so-called fixtures, made of a biocompatible material, preferably pure titanium. The method which has been found to give the highest degree of anchoring stability and which has been used clinically with good results for over 20 years is the so-called osseointegration method developed by Professor Per-Ingvar Brånemark and co-workers. The method is based on a very exact and atraumatic technique for inserting the fixtures in such a way that direct contact, that is exact fitting without an intermediate connective tissue, is achieved between a fixture and a bone tissue. Such direct contact between the fixture and the bone tissue gives the best preconditions for a truly permanent anchoring of a dental prosthesis.

It is also already known to permanently anchor extraoral prostheses. Since 1977, the otology clinic at Sahlgrenska Hospital in Gothenburg has, in collaboration with the Institute of Applied Biotechnology and Nobelpharma AB, been carrying out research on skin-penetrating titanium implants.

The first clinical application was a so-called bone-anchored hearing aid for patients who, for various reasons, cannot use a conventional hearing aid. A screw-shaped titanium implant is introduced by surgery and is allowed to osseointegrate in the bone behind the ear. In a second operation, the titanium screw is exposed and a skin-penetrating element made of titanium is attached. A hearing aid can be mounted on the latter, and via vibrations in the bone, it stimulates the hair cells of the cochlea, see SE-A-431,705.

Another application area for tissue-anchored titanium implants with skin penetration is the attachment of facial prostheses. Nearly seventy patients with defects of the external ear have been provided with prostheses (see Tjellström A, Yontchev E, Lindström J, Brånemark P-I. Five years experience with bone-anchored auricular prostheses. Otolaryngology-Head and Neck Surgery 1985,93, No 3). See also SE-A-450,810 which describes an arrangement for attaching a prosthesis, in particular an auricular prosthesis, in a number of securing elements, implanted in the body tissue, with the aid of a splint.

It is also already known to permanently anchor ocular prostheses (orbital prostheses) in the cranium. For some ten years, patients with orbital defects, for example following tumor surgery, have been treated with good results using tissue-integrated and skin-penetrating implants. See, for example, Jacobsson M, Tjellström A, Thomsen P, Albrektsson T: Integration of titanium implants in irradiated bone tissue; Annals of Otolaryngology, 1986.

After the patient has had the orbit and the floor of the orbit removed, the orbital prosthesis is installed on, for example, three osseointegrated securing elements. The orbital prosthesis can be manufactured with extremely thin edges which permit facial movements without the defect being revealed. This method represents a distinct improvement for the patient, when compared with previous orbital prostheses which were secured on glass eyes.

The implants which have hitherto been used when treating patients with facial prostheses have consisted of a securing element (fixture) anchored in the cranium and a skin-penetrating part which is attached to the securing element, the titanium screw, in a second operation. The securing element (fixture) can consist, for example, of a so-called flange fixture according to Swedish design model No. 42 382.

The skin-penetrating elements (spacing members) which have hitherto been used have been essentially sleeve-shaped and have formed an extension of the securing element in the longitudinal direction thereof. This has caused difficulties in installing the prosthesis, on account of the fact that the accessibility is limited within the orbit. On account of the length of the spacing member there is often an axial/radial lack of space, and this can also be made worse by the non-parallelism of the implants. It is not only the actual installation of the prosthesis, but also the taking of an impression and the fitting of the prosthesis which are made more difficult because of the lack of space arising in the case of the previously used spacing members. The installation of an orbital prosthesis is particularly complicated since the bone quality is often poorer within the orbital area. During installation, it is therefore generally desired to place the securing elements in the radial direction within the essentially circular cavity formed by the orbit, in order to achieve the best bone anchorage. However, from the prosthetics point of view, this is not expedient. For prosthetic work it is instead desirable to have an axial direction of attachment (in the direction of the eye).

It is also important that the spacing members should be designed in such a way that they do not project too far in the axial direction, since this encroaches upon the desired position for the prosthesis. In addition, in order to achieve a good transition between the outer contour of the prosthesis and the face, the prosthesis should, as far as possible, lie recessed within the orbital area.

SUMMARY OF THE INVENTION

The aim of the present invention is to solve the above-mentioned problems and to provide a spacing member which compensates for the non-parallelism and/or axial/radial limit of the implants. The invention is intended in particular to be used with extraoral prostheses in the form of ocular and nasal prostheses, but is not limited to this type of prostheses.

According to the invention, the spacing member comprises a short sleeve-shaped part with a continuous opening for attachment to the upper part (neck) of the securing element and, projecting upwardly from this, an asymmetrical part which forms the attachment point for the prosthesis. The upwardly projecting part (extension part) permits attachment of the prosthesis in a direction which forms essentially a right angle to the direction of the extension part.

Such a design provides favorable direction of attachment, with better space for instruments during the operation and with better space when testing the prosthesis. The direction of orientation of the securing element is not so critical, and instead the securing element can be installed so that the quality of the surrounding bone tissue is as high as possible. The novel spacing member brings together the two apparently conflicting requirements of reliable bone anchorage (radial attachment) and an axial direction of attachment for the prosthetic work. The spacing member furthermore permits a recessing of the prosthesis within the orbital area, which is important from the cosmetic point of view.

BRIEF DESCRIPTION OF THE DRAWINGS

Two different embodiments of the invention are shown diagrammatically in the attached drawings, in which.

DETAILED DESCRIPTION OF THE PREFERRED EMBODIMENTS

Figure 1A:
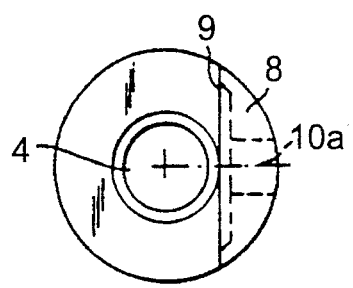
FIGS. 1A–1D show various views of a first variant with a straight, upwardly projecting attachment part for the prosthesis.
Figure 1B:
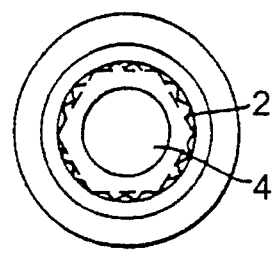
Figure 1C:
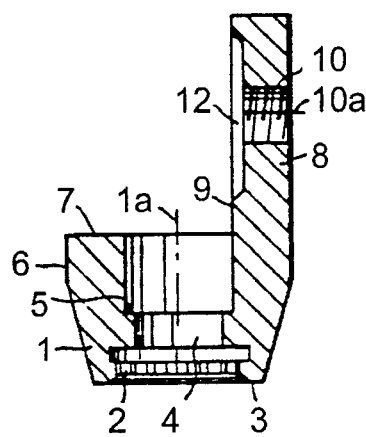
Figure 1D:
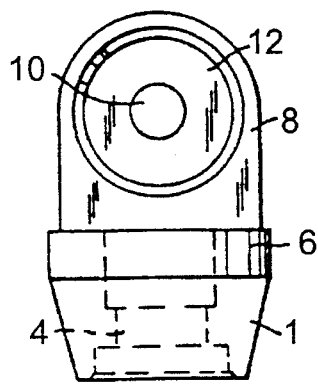

According to FIGS. 1A–1D, the spacing member comprises a conically designed base portion 1 intended to cooperate with the upper portion of a securing element or fixture of the type which has an upper hexagon. Such fixtures are already known and will not therefore be described in more detail here. An example of a fixture which is used in particular in conjunction with extraoral prostheses is illustrated in Swedish design model No. 42 382, a so-called flange fixture. The base portion 1 is arranged in such a way that its line of symmetry 1a coincides with the line of symmetry of the fixture. The base portion is moreover designed with an internal dodecagonal, symmetrical geometry 2, which matches the hexagon of the fixture and gives the spacing member twelve fixed directions of deflection with an angular variation of 30°, and an outer ring-shaped support surface 3 which bears against the shoulder portion of the fixture.

The base portion 1 has a continuous circular hole 4 for a spacing screw (not shown) intended to engage an internally threaded bore in the upper portion of the fixture in order to lock the spacing member securely against the fixture. The head of the spacing screw is intended to bear against an upper, internal circular heel 5 in the hole of the spacing member.

The upper part 6 of the base portion is cylindrical and has a plane end surface 7 from which there projects upwardly and asymmetrically that part 8 forming the attachment point for the prosthesis. This part 8 thus forms a segmental extension of the cylindrical upper part 6 of the base portion and extends parallel to, but on the side of, the line of symmetry 1a of the spacing member. In this way, a bracket-like spacing member is formed, in which the upper plane end surface 7 of the base portion and the inner plane vertical surface 9 form a 90° angle.

Figure 3A:
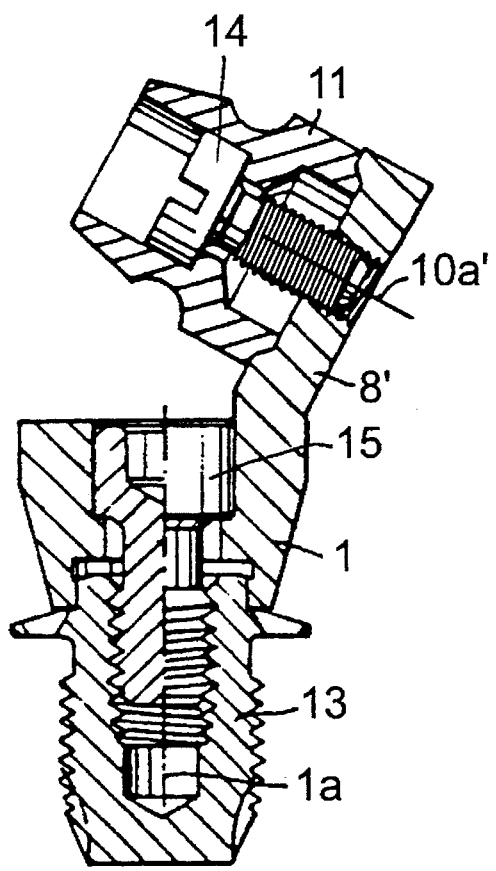
FIGS. 3A–3B show the spacing members are shown screwed together with securing elements and prosthetic sleeves.
Figure 3B:
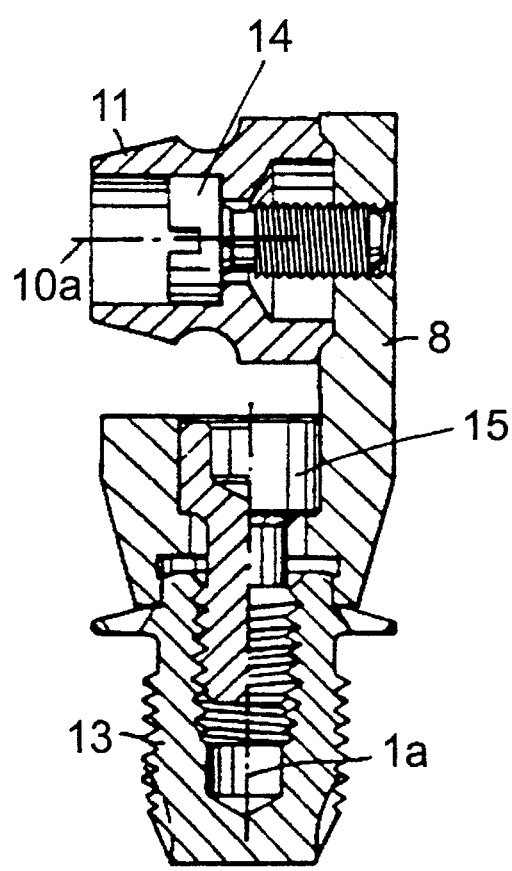

The segmental extension part 8 has a continuous, threaded hole 10 whose line of symmetry 10a forms a right angle to the line of symmetry 1a of the base portion and is intended to receive the screw connection which Joins the extension part 8 to a sleeve 11 embedded in the prosthesis, see FIGS. 3A–3B. The two screw connections for the spacing member to fixture and the spacing member to prosthetic sleeve therefore form in this case a 90° angle, as in the embodiment with the straight extension part 8 shown in FIG. 1. Therefore, present invention is distinct from previously used spacing members where the screw connections were of coaxial orientation, in other word in the line of symmetry of the securing element and in the line of symmetry of the spacing member.

In addition to the fact that the attachment point for the prosthesis has been given a new direction of orientation 10a, the dodecagonal design of the base portion affords the possibility of selecting twelve different directions of deflection within the plane containing the direction 10a.

The inner, planar vertical surface of the segmental extension part is preferably provided with a circular recess 12 which forms a support and backing for the base portion of the sleeve 11 embedded in the prosthesis, see FIGS. 3A–3B.

Figure 2A:
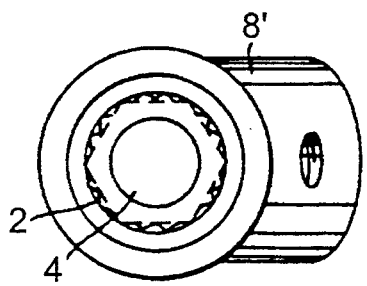
FIGS. 2A–2C show various views of a variant in which the attachment part is at an angle of 30°.
Figure 2B:
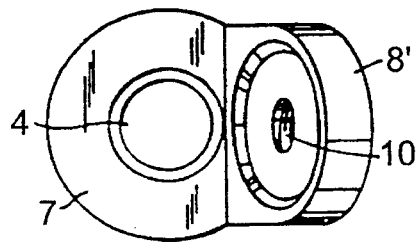
Figure 2C:
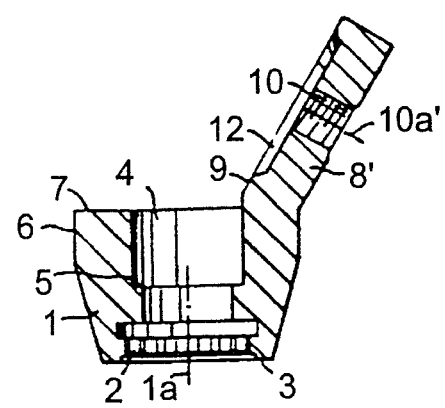

FIGS. 2A–2C shows a second embodiment of spacing members according to the invention, which differs from the embodiment described above in that the extension part 8' has been set at an angle of 30°, in other words the segmental extension part forms an angle of 30° to the line of symmetry 1a of the spacing member. In this case, the line of symmetry 10a' of the second screw connection forms an angle of 120° to the line of symmetry 1a. By setting the extension part at an angle of a desired number of degrees V, it is possible to obtain a radial displacement of the attachment point for the prosthesis and another angle relative to the securing element. By means of a suitable "downward angling" of the extension part 8', it is possible to obtain a lateral displacement and lowering of the attachment point.

FIGS. 3A–3B show the two spacing members joined together with securing element or flange fixture 13 and sleeve 11. Choosing a suitable spacing member, with a straight extension part or with a suitably angled extension part, facilitates the taking of an impression and the fitting and installation of the prosthesis. Instead of working in the line of symmetry 1a where the space is often limited, the novel spacing member allows the attachment point for the prosthesis to be set into two new axes, defined by the line of symmetry 10a, 10a' and a suitable deflection direction.

FIGS. 3A–3B also show the spacing screw 14 of the first screw connection and the screw 15 which fixes the prosthesis sleeve 11 on the extension part.

The invention is not limited to the embodiments shown by way of example, but can be varied within the scope of the patent claims which follow. In particular, the extension part can have different appearances and can form different angles, right down to 90°, with the line of symmetry of the spacing member.

We claim:

1. A craniofacial prosthesis system comprising:

a threaded fixture implantable in the facial bone of a patient, a craniofacial prosthesis, and a spacing member mounted onto a distal portion of said fixture for supporting the craniofacial prosthesis thereon and for connecting the craniofacial prosthesis to the fixture, said spacing member being formed as a unitary member including:

a) a first sleeve-shaped, cylindrical base portion having one end attachable onto said distal portion of the fixture and having a line of symmetry which coincides with a line of symmetry of the fixture, and b) a second portion projecting from an opposite end of said cylindrical base portion and formed as a continuous extension of a part of said cylindrical base portion, said second portion extending in a direction away from said one end of said base portion and forming an acute angle with respect to the line of symmetry of said base portion, said second portion including means for attachment of the craniofacial prosthesis at substantially a 90° angle to said second portion whereby facilitating installation and removal of the craniofacial prosthesis from a facial space in a direction away from the line of symmetry of the fixture.

2. The system according to claim 1, wherein said second portion of said spacing member includes an inner planar surface and an outer surface extending about a portion of and parallel to an outer surface of the sleeve-shaped base portion.

3. The system according to claim 1, wherein said second portion of said spacing member is substantially parallel to the line of symmetry of said base portion.

4. The system according to claim 1, wherein said second portion of said spacing member is angled relative to the line of symmetry of said base portion.

5. The system according to claim 4 wherein said base portion includes indexing means for connecting to an upper end flange of said fixture at a plurality of different fixed positions.

6. The system according to claim 1, wherein said means for attachment includes threaded connection means for securing the craniofacial prosthesis to said second portion.

7. The system according to claim 6, wherein said threaded connection means is at a substantially 90° angle relative to a longitudinal axis of the second portion.

8. A spacing member designed and dimensioned for connecting a craniofacial prosthesis to a fixture implanted in the facial bone of a patient, said fixture having a threaded end for being anchored in said bone and an opposite end, said spacing member comprising an integral member for at least partially projecting outside said facial bone and including:

a) a first sleeve-shaped base portion having a cylindrical wall and having one end attachable onto said opposite end of the fixture, said base having a line of symmetry which generally coincides with a line of symmetry of the fixture, and b) a second portion projecting from an opposite end of said base portion and being formed by upwardly extending a portion of said cylindrical wall in a direction away from said base portion and said fixture, said second portion forming an acute angle with respect to the line of symmetry of said base portion, said second portion including means for attachment of the craniofacial prosthesis at substantially a 90° angle to said second portion whereby facilitating installation of the craniofacial prosthesis in a limited facial space.

9. The system according to claim 8, wherein said second portion of said spacing member includes an inner planar surface and an outer surface extending about a portion of and parallel to an outer surface of the sleeve-shaped base portion.

10. The system according to claim 8, wherein said second portion of said spacing member is substantially parallel to the line of symmetry of said base portion.

11. The system according to claim 8, wherein said means for attachment includes threaded connection means for securing the craniofacial prosthesis to the second portion.

12. The system according to claim 8, wherein said means for attachment includes threaded connection means which is at a substantially 90° angle relative to a longitudinal axis of the second portion.

13. The system according to claim 8, wherein said base portion has indexing means which cooperate with means included on the fixture such that said spacing member may be secured to said fixture in a plurality of different fixed positions.

* * * * *